United States Patent [19]

Fex et al.

[11] 4,150,126

[45] Apr. 17, 1979

[54] NOVEL ENOL ESTERS OF STEROIDS, COMPOSITIONS CONTAINING SUCH COMPOUNDS, PROCESSES FOR THEIR PREPARATION AND METHODS OF TREATMENT THEREWITH

[75] Inventors: Hans Fex; Bertil Hansen, both of Helsingborg; Krister Holmberg, Angelholm; Bertil Högberg; Imre Könyves, both of Helsingborg, all of Sweden

[73] Assignee: Aktiebolaget Leo, Sweden

[21] Appl. No.: 760,151

[22] Filed: Jan. 17, 1977

[30] Foreign Application Priority Data

Feb. 19, 1976 [GB] United Kingdom ................ 6512/76

[51] Int. Cl.$^2$ ............................................. A61K 31/56
[52] U.S. Cl. .................................. 424/238; 424/243; 260/397.4; 260/397.3; 260/397.45; 260/397.5; 260/239.55 D
[58] Field of Search ............. 260/397.4, 397.45, 397.5; 424/238, 243

Primary Examiner—Elbert L. Roberts
Attorney, Agent, or Firm—Gordon W. Hueschen

[57] ABSTRACT

This invention relates to novel enol esters of steroids having an antitumor activity and to the preparation thereof. The invention is also concerned with pharmaceutical compositions containing the said compounds and methods of treatment therewith.

18 Claims, No Drawings

NOVEL ENOL ESTERS OF STEROIDS, COMPOSITIONS CONTAINING SUCH COMPOUNDS, PROCESSES FOR THEIR PREPARATION AND METHODS OF TREATMENT THEREWITH

This invention relates to novel enol esters of steroids, having an antitumour activity, and to the preparation thereof. The invention is also concerned with pharmaceutical compositions containing the said compounds and methods of treatment therewith.

BACKGROUND OF THE INVENTION

Certain carboxylic acids containing a phenyl group substituted with a bis(2-chloroethyl)amino group are well-known antitumour agents.

By reaction of such acids with steroids, having readily esterifiable hydroxyl groups, carboxylic esters have been obtained which, in addition to the antitumour effect exerted by the acid part, may possess valuable hormonal activities, derived from the steroid part. Such esters are described in e.g. J. Med. Chem. 11 (1968) 1106, ibid 12 (1969) 810, ibid 15 (1972) 1158, and U.S. Pat. No. 3,732,260.

The alcohol part of the above-mentioned esters have in the past been restricted to steroids containing hydroxyl groups bound to saturated or aromatic carbon atoms.

A third and very different type of steroid esters are enol esters. It is known that such esters may be prepared through enolisation of carbonyl groups in the steroids, but, to the best of our knowledge, no such enol esters are known which in their acid part contain an alkylating group such as the bis(2-chloroethyl)amino group, neither has any such ester been suggested.

Such esters have now been prepared by us, and it has, moreover, been found that such enol esters of the present invention are highly active against animal tumours. The esters have also been found to have a remarkably low toxicity resulting in very favourable therapeutic indexes.

Depending on the nature of steroid, these compounds also show such pharmacological activities which derive from the steroids themselves, e.g., androgenic, anabolic, gestogenic, and corticoid activities. As many steroids are used in connection with treatment of cancer diseases, the steroid part of the molecule can be selected with relation to the kind of tumor which is to be treated.

The compounds of this invention are therefore of value in the treatment of tumours, especially those situated in organs, which are targets for steroid hormones.

SUMMARY OF THE INVENTION

The new enol esters of steroids of the present invention correspond to the general formula I as defined below.

The compounds of the invention have shown effect in inhibiting the growth of tumors, e.g., Ehrlich ascites, Melanoma Harding-Passey, Hepatoma AH 130, Lymphocytic leukemia (L 1210), and Walker carcinoma 256, according to the procedures set by Cancer Chemotherapy National Service Center (see: Cancer Chemotherapy Reports, January 1959 and December 1962).

The compounds of the invention can be employed in disorders responsive to treatment with antitumour agents and with immunosuppressive agents, as such or combined with either solid or liquid carriers or diluents and made available in varying amounts in such pharmaceutical forms as, e.g., tablets, pills, capsules, pellets, powders, ointments, suppositories, aqueous or non-aqueous suspensions and non-aqueous solutions.

Accordingly, one object of the invention is to provide new compounds, having the general formula I, having the aforesaid activity, preferably also with a relatively low degree of toxicity.

A second object is to provide such type of compounds, which can be employed in disorders responsive to treatment with antitumour agents and with immunosuppressive agents for the amelioration or palliation thereof.

Another object of the invention is to provide processes for preparing the new compounds having the general formula I.

A further object of the invention is to provide a method of treating a living animal body suffering from disorders responsive to treatment with antitumour agents and with immunosuppressive agents, for the amelioration or palliation thereof, which comprises the step of administering to said living animal body a compound having the general formula I, said compound being administered in an amount sufficient to at least mitigate said disorders.

Yet another object of the invention is to provide compositions containing as an active ingredient one or more of the compounds, having the general formula I, preferably together with a pharmaceutically acceptable carrier and, if desired, other pharmacologically active agents.

Accordingly, what we believe and claim to be our invention comprises novel compounds having the general formula:

$$\text{St—R} \qquad \qquad \text{I}$$

wherein R is

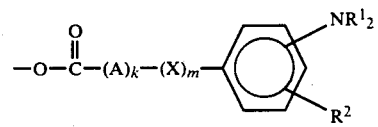

where $R^1$ is a $\beta$- or $\gamma$-halogensubstituted alkyl group having 2 to 4 carbon atoms, the halogen being chlorine or bromine;
where $R^2$ is selected from the group consisting of hydrogen, lower alkyl, lower alkoxy, and halogen;
where A is a straight hydrocarbon chain having at most 4 carbon atoms and being saturated or containing one double bond. At most 2 hydrogen atoms of A may be replaced by lower alkyl and at most one of the hydrogen atoms situated at the carbon atom adjacent to a

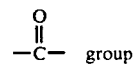

may be replaced by a group selected from the group consisting of amino and lower alkanoylamino;
where X is selected from the group consisting of —O— and —S—;
where k and m are independently selected from the group consisting of zero and one, k always being one when m is one;
wherein St is a residue of a steroid having a cyclopentanophenanthrene carbon-carbon skeleton containing up to a maximum of 40 carbon atoms, inclusive of substituents, said carbon-carbon skeleton including a nucleus which is an unsaturated gonane nucleus having up to a maximum of four double bonds, said steroid residue being attached to R in its 3-position, said position wherein said steroid is attached to R always being situated at the end of an olefinic bond of said gonane nucleus, said position being identified according to steroid nomenclature. Thus, in the compounds of the invention, the substituent R will always be present in the A ring of the steroid in the 3 (three)-position, together with a double bond in one of the 2 (two)- and 3 (three)-positions of the A ring of the steroid.

Thus St is a residue of a steroid in which any hydroxyl group, when present in the steroid molecule, is either free; esterified with a member of the group consisting of carboxylic acids, mono lower alkyl and mono phenyl phosphoric acids, and inorganic polybasic acids; or etherified with an aliphatic or cycloaliphatic alcohol. When esterified with a polybasic acid resulting in one or more acid esters, such acid esters may be in the form of free acids or salts thereof. Any esterifying or etherifying group preferably contains a maximum of 15 carbon atoms.

When St as defined above has hydroxyl groups present in both the 16- and 17-positions, these hydroxyl groups may be in the form of a 16,17-acetonide.

In this disclosure the expression "lower" means that the group referred to contains one to four carbon atoms, inclusive. Thus, lower alkyl, lower alkoxy, and lower alkanoyl include: methyl, ethyl, propyl, iso-propyl, butyl, secondary butyl, iso-butyl, tertiary butyl, methoxy, ethoxy, propoxy, isopropoxy, butoxy, isobutoxy, secondary butoxy, tertiary butoxy, acetyl, propionyl, butyryl, and isobutyryl.

The nomenclature used in this disclosure is in accordance with the I.U.P.A.C. 1957 Rules for Nomenclature of Steroids. Whenever used herein the general formula I and the symbols A, X, R, $R^1$, $R^2$, St, k, and m have the meaning given above.

It is preferred that the halogen atom of $R^1$ is in $\beta$-position and the alkyl group of $R^1$ is ethyl, n-propyl, or n-butyl. Compounds, wherein $R^1$ is —$CH_2$—$CH_2$—Cl are particularly preferred.

The group $NR_2^1$ is preferably in m- or p-position, particularly when k and m are zero, and in p-position when k is one.

It is preferred that $R^2$ is hydrogen or lower alkyl.

When the group $NR_2^1$ is in m-position, it is preferred that $R^2$ is in p-position and different from hydrogen, especially when k and m are zero.

When A is substituted with an amino or a lower alkanoylamino group, it is preferred that m is zero and that A is a saturated chain containing 2 carbon atoms.

It is preferred that m is zero.

X, when present, is preferably oxygen. Said residue, St, of a steroid as defined above has a carbon-carbon skeleton preferably selected from the group consisting of the carbon-carbon skeletons of: 5α-estr-2-ene, 5α-estr-3-ene, estra-3,5-diene, estra-3,5(10)-diene, 5α-androst-2-ene, 5α-androst-3-ene, androsta-3,5-diene, 5α-pregn-2-ene, 5α-pregn-3-ene, pregna-3,5-diene, pregna-1,3,5-triene, pregna-2,4,6-triene, pregna-3,5,7-triene, 19-norpregna-3,5,9-triene, 17α-pregna-3,5-diene, and of 17α-pregna-3,5-dien-20-yne.

Among the carbon-carbon skeletons mentioned above, the following are particularly preferred: the carbon-carbon skeletons of estra-3,5-diene, estra-3,5(10)-diene, 5α-androst-2-ene, 5α-androst-3-ene, androst-3,5-diene, pregna-3,5-diene, and of pregna 1,3,5-triene.

The most particulatly preferred carbon-carbon skeletons are the carbon-carbon skeletons of estra-3,5-diene, 5α-androst-2-ene, androsta-3,5-diene, pregna-3,5-diene, and of pregna-1,3,5-triene.

Preferred nuclei for these types of steroid residues are as follows:
3,17β-dihydroxy-5α-estr-2-ene,
3-hydroxy-5α-estr-2-en-17-one,
3,17β-dihydroxy-5α-estr-3-ene,
3-hydroxy-5α-estr-3-en-17-one,
3,17β-dihydroxyestra-3,5-diene,
3-hydroxyestra-3,5-dien-17-one,
3,17β-dihydroxyestra-3,5(10)-diene,
3-hydroxyestra-3,5(10)-dien-17-one,
3,17β-dihydroxy-5α-androst-2-ene,
3-hydroxy-5α-androst-2-en-17-one,
3,17β-dihydroxy-5α-androst-3-ene,
3-hydroxy-5α-androst-3-en-17-one,
3,17β-dihydroxyandrosta-3,5-diene,
3,11β,17β-trihydroxyandrosta-3,5-diene,
3-hydroxyandrosta-3,5-dien-17-one,
3-hydroxy-5α-pregn-2-en-20-one,
3,17-dihydroxy-5α-pregn-2-en-20-one,
3-hydroxy-5α-pregn-3-en-20-one,
3,17-dihydroxy-5α-pregn-3-en-20-one,
3,17-dihydroxy-17α-pregna-3,5-diene,
3-hydroxypregna-3,5-dien-20-one,
3,17-dihydroxypregna-3,5-dien-20-one,
3,21-dihydroxypregna-3,5-dien-20-one,
3,11β,21-trihydroxypregna-3,5-dien-20-one,
3,11β,17,21-tetrahydroxypregna-3,5-dien-20-one,
3,11β,16α,17,21-pentahydroxypregna-3,5-dien-20-one,
3,21-dihydroxypregna-3,5-dien-11,20-dione,
3,17,21-trihydroxypregna-3,5-dien-11,20-dione,
3,17-dihydroxy-17α-pregna-3,5-dien-20-yne,
3,11β,17,21-tetrahydroxypregna-1,3,5-trien-20-one,
3,11β,16α,17,21-pentahydroxypregna-1,3,5-trien-20-one,
3,17,21-trihydroxypregna-1,3,5-trien-11,20-dione,
3,17-dihydroxypregna-2,4,6-trien-20-one,
3,17-dihydroxypregna-3,5,7-trien-20-one, and
3-hydroxy-19-norpregna-3,5,9-trien-20-one nuclei.

Among the nuclei mentioned above, the following are particularly preferred:
3,17β-dihydroxyestra-3,5-diene,
3,17β-dihydroxyestra-3,5(10)-diene,
3,17β-dihydroxy-5α-androst-2-ene,
3,17β-dihydroxyandrosta-3,5-diene,
3,11β,17β-trihydroxyandrosta-3,5-diene,
3-hydroxypregna-3,5-dien-20-one,
3,17-dihydroxypregna-3,5-dien-20-one,
3,21-dihydroxypregna-3,5-dien-20-one,
3,11β,17,21-tetrahydroxypregna-3,5-dien-20-one,
3,17,21-trihydroxypregna-3,5-dien-11,20-dione,
3,11β,17,21-tetrahydroxypregna-1,3,5-trien-20-one,
3,11β,16α,17,21-pentahydroxypregna-1,3,5-trien-20-one, and
3,17,21-trihydroxypregna-1,3,5-trien-11,20-dione nuclei.

The most particularly preferred nuclei are
3,17β-dihydroxyestra-3,5-diene,
3,17β-dihydroxy-5α-androst-2-en,
3,17β-dihydroxyandrosta-3,5-diene,
3-hydroxypregna-3,5-dien-20-one,
3,17-dihydroxypregna-3,5-dien-20-one, and 3,11β,17,21-tetrahydroxypregna-1,3,5-trien-20-one nuclei.

Said steroid residue, St, has the said steroid nucleus with a hydroxyl group removed from the 3-position thereof; the said radical, R, being attached to said steroid nucleus in said position.

Preferably, any further substitution that is present in the carbon-carbon skeletons of said steroid nuclei, being at most a trisubstitution wherein the positions of the steroid carbon-carbon skeleton which are selected from the positions consisting of the 1-, 2-, 4-, 6-, 7-, 9-, 16-, 17-, 18-, and 21-positions, comprises at least one substituent preferably selected from the group consisting of methyl, ethyl, methylene, allyl, ethynyl, fluoro, and chloro.

When said steroid nucleus has such further substitution it is particularly preferred: that unsaturated estrane skeletons have one or two substituents selected from the group consistng of 17α-ethyl, 17α-allyl, 17α-ethynyl, and 18-methyl; that unsaturated androstane skeletons have one or two substituents selected from the group consisting of 2-methyl, 4-methyl, 6-methyl, 7α-methyl, 9α-fluoro, and 17α-methyl; that unsaturated pregnane and norpregnane skeletons have one of more, but at most three, substituents selected from the group consisting of 1,2-methylene, 6-fluoro, 6-chloro, 6-methyl, 9α-fluoro, 16-methyl, 16-methylene, 17-methyl, and 21-methyl.

Preferred steroid residues, St, are the following: Androgen related, when the living animal body suffers from cancer diseases known to be responsive to treatment with androgen hormones, preferably
17β-hydroxyestra-3,5-diene,
17α-ethyl-17β-hydroxyestra-3,5-diene,
17α-hydroxy-5α-androst-2-ene,
17β-hydroxy-5α-androst-2-ene,
5α-androst-2-en-17-one,
17β-hydroxy-2-methyl-5α-androst-2-ene,
17β-hydroxy-4-methyl-5α-androst-3-ene,
17β-hydroxy-6α-methyl-5α-androst-2-ene,
17β-hydroxy-6β-methyl-5α-androst-2-ene,
17β-hydroxy-17α-methyl-5α-androst-2-ene,
17β-hydroxyandrosta-3,5-diene,
androsta-3,5-dien-17-one,
17β-hydroxy-4-methylandrosta-3,5-diene,
17β-hydroxy-6-methylandrosta-3,5-diene,
17β-hydroxy-17α-methylandrosta-3,5-diene,
17β-hydroxy-7α,17α-dimethylandrosta-3,5-diene,
9α-fluoro-11β,17β-dihydroxy-17α-methylandrosta-3,5-diene, and
17-hydroxy-17α-pregna-3,5-diene residues.

Among the androgen related steroid residues mentioned above, the following are particularly preferred:
17β-hydroxyestra-3,5-diene,
17β-hydroxy-5α-androst-2-ene,
17β-hydroxyandrosta-3,5-diene,
17β-hydroxy-17α-methylandrosta-3,5-diene, and
9α-fluoro-11β,17β-dihydroxy-17α-methylandrosta-3,5-diene residues.

The following androgen related steroid residues are most particularly preferred:
17β-hydroxyestra-3,5-diene,
17β-hydroxy-5α-androst-2-ene, and
17β-hydroxyandrosta-3,5-diene residues.

Gestogen related, when the living animal body suffers from cancer diseases known to be responsive to treatment with gestogen hormones, preferably
17α-ethynyl-17β-hydroxyestra-3,5-diene,
17α-allyl-17β-hydroxyestra-3,5-dien,
17α-ethynyl-17β-hydroxy-18-methylestra-3,5-diene,
17α-ethynyl-17β-hydroxyestra-3,5(10)-diene,
17-hydroxy-17α-pregna-3,5-dien-20-yne,
pregna-3,5-dien-20-one,
17-hydroxypregna-3,5-dien-20-one,
17-hydroxy-6-methylpregna-3,5-dien-20-one,
17-hydroxy-6-methylpregna-2,4,6-trien-20-one,
6-chloro-17-hydroxypregna-2,4,6-trien-20-one,
17-hydroxy-16-methylenepregna-2,4,6-trien-20-one,
6-chloro-17-hydroxy-16-methylenepregna-2,4,6-trien-20-one,
17-hydroxy-6-methylpregna-3,5,7-trien-20-one,
6-chloro-17-hydroxypregna-3,5,7-trien-20-one,
17-hydroxy-16-methylenepregna-3,5,7-trien-20-one,
6-chloro-17-hydroxy-16-methylenepregna-3,5,7-trien-20-one,
17,21-dimethyl-19-norpregna-3,5,9-trien-20-one, and
6-chloro-17-hydroxy-1α,2α-methylenepregna-3,5,7-trien-20-one residues.

Among the gestogen related steroid residues mentioned above, the following are particularly preferred:
17α-ethynyl-17β-hydroxyestra-3,5-diene,
17α-ethynyl-17β-hydroxyestra-3,5(10)-diene,
pregna-3,5-dien-20-one, and
17-hydroxypregna-3,5-dien-20-one residues.

Corticoid related, when the living animal body suffers from cancer or autoimmune diseases known to be responsive to treatment with corticoid hormones, preferably
21-hydroxypregna-3,5-dien-20-one,
11β,21-dihydroxypregna-3,5-dien-20-one,
21-hydroxypregna-3,5-diene-11,20-dione,
17,21-dihydroxypregna-3,5-diene-11,20-dione,
11β,17,21-trihydroxypregna-3,5-dien-20-one,
9α-fluoro-11β,17,21-trihydroxypregna-3,5-dien-20-one,
6-fluoro-11β,16α,17,21-tetrahydroxypregna-3,5-dien-20-one,
17,21-dihydroxypregna-1,3,5-triene-11,20-dione,
11β,17,21-trihydroxypregna-1,3,5-trien-20-one,
11β,17,21-trihydroxy-6-methylpregna-1,3,5-trien-20-one,
11β,17,21-trihydroxy-16-methylenepregna-1,3,5-tiren-20-one,
6-fluoro-11β,17,21-trihydroxy-16α-methylpregna-1,3,5-trien-20-one,
6-fluoro-11β,16α,17,21-tetrahydroxypregna-1,3,5-trien-20-one,
9α-fluoro-11β,17,21-trihydroxy-16α-methylpregna-1,3,5-trien-20-one,
9α-fluoro-11β-17,21-trihydroxy-16β-methylpregna-1,3,5-trien-20-one,
9α-fluoro-11β,16α,17,21-tetrahydroxypregna-1,3,5-trien-20-one,
6,9α-difluoro-11β,17,21-trihydroxy-16α-methylpregna-1,3,5-trien-20-one,
6,9α-difluoro-11β,16α,17,21-tetrahydroxypregna-1,3,5-trien-20-one, and
6-fluoro-11β,17,21-trihydroxy-16-methylenepregna-1,3,5-trien-20-one residues.

Among the corticoid related steroid residues mentioned above, the following are particularly preferred:
21-hydroxypregna-3,5-dien-20-one,
17,21-dihydroxypregna-3,5-diene-11,20-dione,
11β,17,21-trihydroxypregna-3,5-dien-20-one,
17,21-dihydroxypregna-1,3,5-trien-11,20-dione,
11β,17,21-trihydroxypregna-1,3,5-trien-20-one, 9α-fluoro-11β,17,21-trihydroxy-16α-methylpregna-1,3,5-trien-20-one,
9α-fluoro-11β,17,21-trihydroxy-16β-methylpregna-1,3,5-trien-20-one, and
9α-fluoro-11β,16α,17,21-tetrahydroxypregna-1,3,5-trien-20-one residues.

Most particularly preferred corticoid related steroid residues are the following:
21-hydroxypregna-3,5-dien-20-one,
17,21-dihydroxypregna-3,5-dien-11,20-dione,
11β,17,21-trihydroxypregna-3,5-dien-20-one,
17,21-dihydroxypregna-1,3,5-trien-11,20-dione, and
11β,17,21-trihydroxypregna-1,3,5-trien-20-one residues.

When one or more hydroxyl groups are connected to non-olefinic carbon atoms of the steroid skeleton of St, as mentioned above, that is non-enolic hydroxyl groups, it is preferred that such hydroxyl groups are esterified or etherified, especially esterified; particularly such hydroxyl groups, which are positioned in one or more of the 16-, 17-, and 21-positions are preferred to be esterified or etherified.

Among acids which can be used to form esters with one or more of said hydroxyl groups, the following are preferred: Alkane monocarboxylic acids having at most ten carbon atoms, such as acetic acid, propionic acid, valeric acid, dimethylpropanoic acid, hexanoic acid, heptanoic acid, decanoic acid, and cyclohexanecarboxylic acid.

Especially preferred are lower alkane monocarboxylic acids such as acetic acid and propionic acid.

Alkane dicarboxylic acids having at most four carbon atoms, such as succinic acid.

Aromatic carboxylic acids such as benzoic acid.

Inorganic polybasic acids such as phosphoric acid and sulfuric acid.

To obtain lipophilic esters the following acids are especially preferred: Valeric acid, hexanoic acid, heptanoic acid, and decanoic acid.

To obtain hydrophilic esters having acid ester groups the following acids are especially preferred: succinic acid and phosphoric acid.

Among alcohols which can be used to form ethers with one or more of said hydroxyl groups, the following are preferred: aliphatic and cycloaliphatic alcohols containing at most six carbon atoms, such as methanol, ethanol, cyclopentanol, and cyclohexanol.

Particularly preferred alcohols among those given above are methanol and cyclopentanol.

When St above contains one or more hydroxyl groups esterified with a polybasic acid, any remaining acid group or groups are preferably in the form of pharmaceutically acceptable salts with suitable inorganic or organic cations, such as those derived from the following metals and amines:

metals: calcium, potassium, and sodium
amines: monoethanolamine, diethanolamine, dimethylaminoethanol, N-methylglucamine, trishydroxymethylmethylamine, morpholine, and the like.

In the following, references to the literature are given by elevated, underlined, numbers, e.g., "this method[17] is". The numbers refer to literature sources listed after the examples.

Methods of Preparation

The compounds having structure I may be prepared by conventional methods.

A general process (method 1 below) for preparing compounds having structures I is as follows:

Method 1

Compound I is prepared by reacting an acid II, or a reactive derivative thereof, and a steroid B, which is the keto form of the compound St-OH, the latter being the alcohol part of ester I.

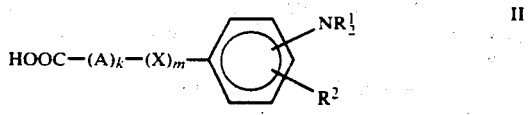

In the following, B has the meaning given above.

Among other methods for preparing compounds having structure I, the following may be mentioned.

Method 2

Reaction of a steroid enol ester III and acid II, or a reactive derivative thereof, provides I.

$$St-O-Z-R^3 \quad\quad III$$

In structure III and in the following Z means a member of the group consisting of

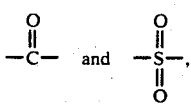

and $R^3$ means a member of the group consisting of lower alkyl, optionally substituted with fluorine or chlorine, and phenyl, optionally substituted with a member of the group consisting of lower alkyl, chlorine, and bromine.

Method 3

Compound I, wherein k and m are one, is prepared by reaction of a steroid enol ester IV and a compound V, or a reactive derivative thereof.

$$St-O-\overset{O}{\underset{\|}{C}}-R^4 \quad\quad IV$$

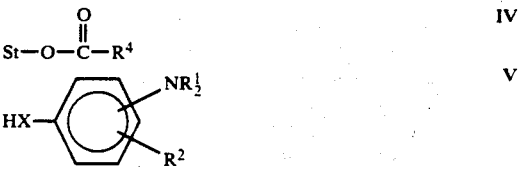

In structure IV and in the following, $R^4$ means a group which, together with the group —HX of compound V, or a reactive derivative thereof, in one or more steps, can form the group —A—X—.

In synthesizing compounds having structure I by any of the methods mentioned above each group of the starting materials involved must be compatible with the process in question or, if necessary, protected during one or more reaction steps and then converted to the desired group.[1,2] Pertinent examples of groups that may be protected are hydroxyl and carbonyl groups in the steroid and an amino group of A.

Examples of protective groups for carbonyl groups in the steroid are ketals, e.g. 1,3-dioxolans, hemithioketals, e.g. 1,3-oxathiolans, and dithioketals, e.g. 1,3-dithiolans. 1,3-Dioxolan derivatives may be prepared by treatment of carbonyl compounds with ethylene glycol in the presence of an acid catalyst,[8] and the carbonyl groups may be regenerated upon treatment with acids, such as hydrochloric acid in acetone.[2] 1,3-Oxathiolans may be formed by acid-catalyzed reaction between 2-mercaptoethanol and carbonyl compounds,[10] and they may be reconverted into ketones by treatment with acids, such as hydrochloric acid in dioxan,[11] or by the action of Raney nickel.[9] 1,3-Dithiolans may be prepared by acid-catalyzed reaction of carbonyl compounds with ethanedithiol,[10] and the carbonyl functions may subsequently be regenrated by the action of mercuric salts.[12]

Examples of protective groups for hydroxyl groups in the steroids are ethers, e.g., tert.-butyldimethylsilyl ethers or methylthiomethyleters. Tert.-butyldimethylsilyl ethers may be prepared by reaction of tert.-butyldimethylsilyl chloride with alcohols,[17] and the hydroxyl groups may be regenerated by treatment with tetrabutylammonium fluoride in tetrahydrofuran.[17] Methylthiomethyl ethers may be prepared by reaction of sodium alkoxides in dimethoxyethane with iodomethyl methyl sulfide, formed in situ from chloromethyl methyl sulfide and sodium iodide.[18] The converof methylthiomethyl ethers to alcohols may be effected by reaction with mercuric chloride in acetonitrile-water or reaction with silver nitrate in tetrahydrofuran-water.[18]

Examples of protective groups for an amino group of A are substituted or unsubstituted benzyloxycarbonyl and benzyl groups. Such N-benzyloxycarbonyl derivatives may be prepared by reaction of amino compounds with benzyl chloroformate in the presence of an alkaline catalyst,[13] and the amino group may subsequently be regenerated by treatment with acidic reagents, such as hydrogen chloride[14] or by catalytic hydrogenation.[15] Mono-N-benzyl derivatives may be synthesized by treatment of amines with benzyl chloride in the presence of base and subsequent partial hydrogenation of the dibenzyl compounds formed;[16] debenzylation may be achieved by catalytic hydrogenation.

It is understood that one or more of the steps described in the methods 1–3 above may be carried out with one or both of the halogen atoms of $R^1$ replaced by groups, e.g. hydroxyl or sulfonic esters thereof, which subsequently can be substituted by Hal, thus providing the desired compound.

Methods 1–3 above are illustrated by the following processes (a–c):

(a) A process according to method 1, characterized by reacting, in one or more steps, steroid B and acid II, or a reactive derivative thereof, preferably in the presence of a catalyst or an anhydride.

Examples of reactive derivatives of acid II are its anhydride, mixed anhydride, and acyl halide, for instance, acyl chloride.

Suitable catalysts are, for instance, strong organic or inorganic acids, such as arylsulfonic acids or perchloric acid. A suitable anhydride is, for instance, trifluoroacetic anhydride.

(b) A process according to method 2, characterized by reacting, in one or more steps, steroid enol ester III and acid II, or a reactive derivative thereof, preferably in the presence of a catalyst.

Compound II is preferably in the form of the free acid. Suitable catalysts are, e.g., strong acids, such as perchloric acid or arylsulfonic acids, metal salts, such as mercuric oxide,[3] or combinations of strong acids and metal salts, such as a mixture of mercuric acetate and sulfuric acid.[4]

Ester III may be prepared by known methods, e.g. by reacting steroid B and acid VI, or a reactive derivative thereof, such as its anhydride, acyl halide, or ester with lower alkenols, preferably in the presence of an anhydride, such as trifluoroacetic anhydride, or a catalyst, e.g., a strong organic or inorlganic acid, such as an arylsulfonic acid or perchloric acid VI having the formula:

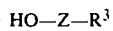  VI wherein Z and $R^3$ are hereinbefore defined.

(c) A process according to method 3, characterized by reacting, in one or more steps, steroid enol ester IV and compound V, or a reactive derivative thereof, with or without a catalyst.

Ester IV may be prepared by known methods, for example, by reacting steroid B and acid VII, or a reactive derivative thereof such as its anhydride or acyl halide, preferably in the presence of an anhydride, such as trifluoroacetic anhydride, or a catalyst, e.g., a strong organic or inorganic acid, such as an arylsulfonic acid or perchloric acid.

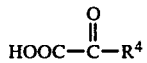  VII

The group $R^4$ may be an alkyl halide or a vinyl group.

Examples of reactive derivatives of compound V when $R^4$ is an alkyl halide are ion pairs, obtained, e.g., by using an equvalent or a catalytic amount or a quaternary ammonium cation as counterion,[5] and metal salts of for instance silver or an alkali metal.[6]

When $R^4$ is a vinyl group, the reaction between compounds IV and V is of the cyanoethylation type,[7] and the reaction is preferably performed in the presence of an alkaline catalyst, such as pyridine or an alkali metal.

The compounds of the invention are generally characterized by the pharmacological activity hereinbefore stated, making them useful in counteracting certain physiological abnormalities in a living animal body. Effective quantities of the pharmacologically active compounds of the invention may be administered to a living animal body in any one of various ways, for example orally as in capsules or tablets, parenterally in the form of sterile solutions, suspensions, and by pellet implantation. Among routes of parenteral administration are intravenously, subcutaneously, intramuscularly, intraperitoneally, intraarticularly, and intradermally. Other modes of administration are vaginally, rectally, and topically as e.g., in the form of ointments, suppositories, and powders.

As representative of living animal bodies, which may be treated with the compounds and compositions of the invention, and according to the method of treatment of the invention, for alleviation of the same and/or similar conditions as those described, in addition the following may be mentioned: domestic animals such as dogs and cats and farm animals such as horses, cows, sheep, and goats.

Pharmaceutical formulations are usually prepared from a predetermined quantity of one or more of the compounds of the invention. Such formulations may take the form of powder, syrups, suppositories, ointments, solutions, pills, capsules, pellets or tablets, suspensions, emulsions, oil solutions, etc., with or without, but preferably with, any one of a large variety of pharmaceutically acceptable vehicles or carriers. When in a mixture with a pharmaceutical vehicle or carrier, the active ingredient usually comprises from about 0.01 to about 75 percent, normally from about 0.05 to about 15 percent, by weight of the composition. Carriers such as starch, sugar, talc, commonly used synthetic and natural gums, water, and the like, may be used in such formulations. Binders such as polyvinylpyrrolidone and lubricants such as sodium stearate, may be used to form tablets. Disintegrating agents such as sodium carbonate may also be included in tablets.

Although relatively small quantities of the active materials of the invention, even as low as 5.0 milligrams, may be used in cases of administration to subjects having a relatively low body weight, unit dosages are preferably five milligrams or above and preferably twenty-five, fifty, or one hundred milligrams, or even higher, depending of course upon the subject treated and the particular result desired, as will be apparent to one skilled in the art. Broader ranges appear to be 1 to 1000 milligrams per unit dose.

The active agents of the invention may be combined for administration with other pharmacologically active agents such as analgesics, steroids or hormones, or the like, or with buffers, antacids or the like, and the proportion of the active agent or agents in the compositions may be varied widely. It is only necessary that the active ingredient of the invention constitute an effective amount, i.e., such that a suitable effective dosage will be obtained consistent with the dosage form employed. Obviously, several unit dosage forms may be administered at about the same time. The exact individual dosage as well as daily dosages in a particular case will of course be determined according to well established medical and/or veterinary principles under the supervision of the physician or veterinarian in charge. As a rule, however, when used therapeutically, the present compounds may be administered in a quantity of 1 to 1000 milligrams, preferred ranges being 2-100 milligrams per day and subject or patient, divided in 1 to 4 or more doses, over a suitable period and depending upon the subject and the type of subject being treated.

The following examples are intended to illustrate but not to limit the scope of the invention, although the compounds named are of particular interest for our intended purposes. These compounds have been designated by underlined numbers which are used in the biological examples below. The NMR data given in the examples are obtained from solutions in deuterated chloroform using a 60 MHz instrument (Perkin-Elmer R 12).

EXAMPLE 1

A mixture of 4-/4-(N,N-bis(2-chloroethyl)amino)-phenyl/butanoic anhydride (82.6 g), 17-acetoxypregn-4-ene-3,20-dione (18.6 g), and 4-toluenesulfonic acid (3.8 g) is heated at 100° C. under nitrogen for 3 h and then poured into a mixture of pyridine (200 ml) and ice (60 g). After 3 h, 5 M HCl (1000 ml) is added under cooling, and the solution is extracted with 1:1 mixture of ethyl acetate/ether (3×500 ml). The organic phase is washed with aq. 0.5 M $K_2CO_3$ and $H_2O$, dried, and evaporated to give an oil which is chromatographed on a silica gel column using toluene/ethyl acetate (2:1) as eluent. The eluate fraction having $R_f=0.5$ yields 17-acetoxy-3-/4-(4-(N,N-bis(2-chloroethyl)amino)phenyl)-butanoyloxy/pregna-3,5-dien-20-one (1), m.p. 151°–2° C. after recrystallization from ether/hexane.

The structure is confirmed by NMR, IR, and analysis for Cl and N. The siginficant signals of the NMR spectrum are the following: δ (ppm) 0.67 (s, 3H, H-18), 1.02 (s, 3H, H-19), 1.04 and 1.11 (singlets, 3H each, 2-$COCH_3$), 3.68 (s, 8H, 2-$CH_2CH_2Cl$), 5.42 (broad s, 1H, H-6), 5.72 (broad s, 1H, H-4), 6.70 and 7.09 (doublets with J=9 Hz, 2H each, aromatic H).

In substantially the same manner the following compounds are obtained from the corresponding starting materials. The structures of the compounds are confirmed as above.

2. 3-/4-(4-(N,N-bis(2-chloroethyl)amino)phenyl)-butanoyloxy/pregna-3,5-dien-20-one,
3. 17β-acetoxy-3-/4-(N,N-bis(2-chloroethyl)amino)-phenyl)acetoxy/androsta-3,5-diene,
4. 17β-acetoxy-3-/3-(4-(N,N-bis(2-chloroethyl)amino)-phenoxy)propanoyloxy/-17α-methylandrosta-3,5-diene,
5. 11β,17β-diacetoxy-3-/4-(N,N-bis(2-chloroethyl)amino)phenylthioacetoxy/-9α-fluoro-17α-methylandrosta-3,5-diene,
6. 17β-acetoxy-3-/3-(N,N-bis(2-chloropropyl)amino)-4-methylbenzoyloxy/-7α,17α-dimethyl-androsta-3,5-diene,
7. 17β-acetoxy-17α-allyl-3-/5-(4-(N,N-bis(2-chloroethyl)amino)phenyl)pentanoyloxy/estra-3,5-diene,
8. 17β-acetoxy-3-/3-(2-(N,N-bis(2-chloroethyl)amino)-phenylpropenoyloxy/-17α-ethynyl-18-methylestra-3,5-diene,
9. 21-acetoxy-3-[2-(4-(N,N-bis(2-chloroethyl)amino)-phenyl)-2-methylpropanoyloxy]-6-fluoro-11β-hydroxy-16α,17-isopropylidendioxypregna-3,5-dien-20-one,
10. 3-[4-(4-(N,N-bis(2-chloroethyl)amino)phenyl)-butanoyloxy]-17β-propanoyloxyestra-3,5-diene,
11. 17β-acetoxy-3-[4-(4-(N,N-bis(2-chloroethyl)amino)-phenyl)butanoyloxy]androsta-3,5-diene,
12. 17β-acetoxy-3-[4-(4-(N,N-bis(2-chloroethyl)amino)-phenyl)butanoyloxy]androst-2-ene,
13. 3-[(2S)-2-acetamido-3-(4-(N,N-bis(2-chloroethyl)amino)phenyl)propanoyloxy]-17β-propanoyloxyandrosta-3,5-diene,
14. 17-acetoxy-3-[4-(N,N-bis(2-chloroethyl)amino)-phenylacetoxy]pregna-3,5-dien-20-one,
15. 17,21-diacetoxy-3-[4-(4-(N,N-bis(2-chloroethyl)amino)phenyl)butanoyloxy]pregna-3,5-dien-11,20-dione,
16. 17,21-diacetoxy-3-[4-(4-(N,N-bis(2-chloroethyl)amino)phenyl)butanoyloxy]-pregna-3,5-dien-20-one, and
17. 21-acetoxy-3-[4-(4-(N,N-bis(2-chloroethyl)amino)-phenyl)butanoyloxy]-pregna-3,5-dien-20-one.

EXAMPLE 2

To a mixture of 3-/N,N-bis(2-chloroethyl)amino/-4-methylbenzoic acid (26.2 g) and trifluoroacetic anhydride (21.0 g) 17β-acetoxy-5α-androstan-3-one (16.6 g) is added. After 24 h at room temperature toluene is added and the solution is washed with $H_2O$, aq $NaHCO_3$, and $H_2O$. Drying and evaporation gives an oil which is chromatographed on a silica gel column using toluene/ethyl acetate (2:1) as eluent. The eluate fraction having $R_f=0.5$ yields 17β-acetoxy-3-/3-(N,N-bis(2-chloroethyl)amino)-4-methylbenzoyloxy/androst-2-ene (1).

The structure is confirmed by NMR, IR, and analysis for Cl and N. The significant signals of the NMR spectrum are the following: δ (ppm) 0.79 and 0.81 (singlets, 3H each, H-18 and H-19), 2.02 (s, 3H, —$COCH_3$), 3.42 (s, 8H, 2-$CH_2CH_2Cl$), 4.63 (broad t, 1H, H-17), 5.18 (broad s, 1H, H-2), 7.27 and 7.78 (doublets with J=8, 1H each, aromatic H), 7.87 (s, 1H, aromatic H).

In substantially the same manner the following compounds are obtained from the corresponding starting materials. The structures of the compounds are confirmed as above.

2. 17β-acetoxy-3/4-(4-(N,N-bis(2-chloroethyl)amino)phenyl)butanoyloxy/-17α-ethynylestra-3,5-diene,
3. 3-/3-(N,N-bis(2-chloroethyl)amino)-4-methylbenzoyloxy/-17β-methoxyestra-3,5-diene,
4. 17β-acetoxy-3-/3-(N,N-bis(2-chloroethyl)amino)benzoyloxy/-17α-ethylestra-3,5-diene,
5. 3-/5-(4-(N,N-bis(2-chloroethyl)amino)phenyl)pentanoyloxy/-2-methyl-17β-propanoyloxyandrost-2-ene,
6. 3-/3-(N,N-bis(2-bromoethyl)amino)-4-methylbenzoyloxy/-17β-hexanoyloxy-4-methylandrost-3-ene,
7. 17β-acetoxy-3-/3-(N,N-bis(2-chloroethyl)amino)-4-methylbenzoyloxy/-17α-ethynylestra-3,5(10)-diene,
8. 3-/3-(N,N-bis(2-chloroethyl)amino)-4-methylbenzoyloxy/-21-cyclopentyloxypregna-3,5-dien-20-one,
9. 3-/3-(4-(N,N-bis(2-chloroethyl)amino)phenoxy)-propanoyloxy/-17,21-dipropanoyloxypregna-3,5-dien-11,20-dione,
10. 11β,17,21 -triacetoxy-3-/4-(N,N-bis(2-chloroethyl)amino)phenylacetoxy/-pregna-3,5-dien-20-one,
11. 17-acetoxy-3-[3-(N,N-bis(2-chloroethyl)amino)-4-methylbenzoyloxy]pregna-3,5-dien-20-one, and
12. 17-acetoxy-3-[4-chloro-3-(N,N-bis-(2-chloroethyl)amino)benzoyloxy]pregna-3,5-dien-20-one.

EXAMPLE 3

A mixture of 17-acetoxy-16-methylenepregna-4,6-dien-20-one (19.1 g), 3-/N,N-bis(2-chloroethyl)amino/-4-methylbenzoyl chloride (24.4 g), and pyridine (80 ml) is heated at 50° C. for 4 h. After cooling, the reaction mixture is poured into ice-water and the solution is extracted with a 1:1 mixture of toluene/ethyl acetate (3×100 ml). The combined extracts are washed with 2 M HCl, H$_2$O, aq NaHCO$_3$, and H$_2$O, dried and evaporated to give an oil which is chromatographed on a silica gel column using toluene/ethyl acetate 2:1 as eluent. The eluate fraction having R$_f$=0.5 gives 17-acetoxy-3-/3-(N,N-bis(2-chloroethyl)amino-4-methylbenzoyloxy/-16-methylenepregna-3,5,7-trien-20-one (1).

The structure is confirmed by NMR, IR, and analysis for Cl and N. The significant signals of the NMR spectrum are the following: δ (ppm) 0.76 (s, 3H, H-18), 1.12 (s, 3H, H-19), 2.05 and 2.15 (singlets, 3H each, 2-COCH$_3$), 3.43 (s, 8H, 2-CH$_2$CH$_2$Cl), 5.35–6.30 (broad signals, 5H, H-4+H-6++H-7+CH$_2$-16), 7.27 and 7.77 (doublets with J=8, 1H each, aromatic H), 7.85 (s, 1H, aromatic H).

In substantially the same manner the following compounds are obtained from the corresponding starting materials. The structures of the compounds are confirmed as above.

2. 17-benzoyloxy-3-/4-(N,N-bis(2-chloroethyl)amino)phenylacetoxy/-6-methylpregna-3,5,7-trien-20-one,
3. 17-acetoxy-6-chloro-3-[4-(4-(N,N-bis(2-chloroethyl)amino)phenyl)butanoyloxy]-1α,2α-methylenepregna-3,5,7-trien-20-one,
4. 11β,17,21-triacetoxy-3-/3-(N,N-bis(2-chloropropyl)amino)-4-methylbenzoyloxy/-9α-fluoro-16β-methylpregna-1,3,5-trien-20-one,
5. 17,21-diacetoxy-3-/4-(N,N-bis(2-chloroethyl)amino)phenylthioacetoxy/pregna-1,3,5-trien-11,20-dione,
6. 11β,17,21-triacetoxy-3-/4-(4-(N,N-bis(2-chloroethyl)amino)phenyl)butanoyloxy/pregna-1,3,5-trien-20-one,
7. 11β,17,21-triacetoxy-3-/3-(N,N-bis(2-bromoethyl)amino)-4-methylbenzoyloxy/-9α-fluoro-16α-methylpregna-1,3,5-trien-20-one,
8. 11β,21-diacetoxy-3-/3-(2-(N,N-bis(2-chloroethyl)amino)phenyl)propenoyloxy/-9α-fluoro-16α,17-isopropylidendioxypregna-1,3,5-trien-20-one,
9. 3-[4-(4-(N,N-bis(2-chloroethyl)amino)phenyl)butanoyloxy]androsta-3,5-dien-17β-phosphate, and
10. 3-[3-(N,N-bis(2-chloroethyl)amino)-4-methylbenzoyloxy]androsta-3,5-dien-17β-phosphate.

EXAMPLE 4

This example illustrates the effect of the compounds of the general formula I in inhibiting the growth of tumours.

LD50 is the dose that causes a 50 percent lethality of the animals, and ED50 is the dose that causes a 50 percent reduction of tumour size.

From the data below it is obvious that the compounds have a very low toxicity, and that the therapeutic indexes (T.I.), i.e. the ratios LD50/ED50, are very high.

The experimental design is in accordance with the standards set by the CCNSC (Cancer Cheomotherapy Reports, January 1959 and December 1962).

Some of the results obtained are given in Tables 1 and 2 below. The compounds are named by a number code, a:b, where a means the example, wherein the preparation of the comound in question is described, and b refers to the order of the compounds prepared according to that example. Thus, compound 1:2 means the second compound prepared according to Example 1. The systematic names of the compounds are given in the examples.

This example shows that the new compounds are useful to interfere with and suppress the growth of tumours and in some cases even cause up to complete remission of tumours and therefore can be employed in treating a living animal body suffering from disorders responsive to treatment with anti-cancer agents and with immunosuppressive agents.

Table 1.

| Walker carcinosarcoma 256 | | | |
| --- | --- | --- | --- |
| Experimental animals: Sprague-Dawley rats. | | | |
| Tumour implant: Tumour pieces with 2–4 mm diameter, subcutaneously. | | | |
| Therapy: Daily p.o. administration for 5 days starting on the day following implantation. | | | |
| Termination: The animals are killed on the 9th day. | | | |
| Evaluation: Weights of tumours of test animals are compared with those of control animals. | | | |
| Preliminary results: | | | |
| Compound | LD50 | ED50 | T.I. |
| 1:1 | >5 × 250 | 5 × 2 | >125 |
| 1:2 | 5 × 125 | 5 × 1.5 | 83 |
| 2:2 | 5 × 20 | 5 × 0.5 | 40 |
| 1:11 | 5 33 150 | 5 × 3 | 50 |
| 1:12 | 5 × 150 | 5 × 1 | 150 |
| 1:14 | 5 × 250 | 5 × 2 | >125 |
| 1:16 | >5 × 125 | 5 × 4 | >30 |

The following additional compounds exhibit antitumour activity in the foregoing test: 1:3–1:9, 2:1, 2:3–2:11, and 3:1–3:8.

Table 2.

| Hepatoma AH 130 |
| --- |
| Experimental animals: Sprague-Dawley rats. |
| Tumour implant: 5 × 10$^6$ tumour cells i.p. |
| Therapy: One injection i.p. on the day following implantation. |

Table 2.-continued

Hepatoma AH 130

Termination: The animals are killed on the 8th day.
Evaluation: Weights of tumours of test animals are compared with those of control animals.
Preliminary results:

| Compound | LD50 | ED50 | T.I. |
|---|---|---|---|
| 1:2 | 1 × 800 | 1 × 60 | 13 |
| 2:2 | >1 × 250 | 1 × 25 | >10 |
| 2:11 | >1 × 250 | 1 × 50 | >5 |
| 1:11 | >1 × 250 | 1 × 20 | >12 |
| 1:12 | >1 ×250 | 1 × 30 | >8 |
| 1:14 | >1 ×250 | 1 × 8 | >30 |

The following additional compounds exhibit anti-tumour activity in the foregoing test: 1:1, 1:8–1:10, 1:13, 1:15–1:17, 2:9–2:10, and 3:5–3:10.

Table 3.

Ehrlich ascites tumour, ELD hyperdiploid (46 chromosomes)

Experimental animals: SPF NMRI mice.
Tumour implant: $2 \times 10^6$ tumour cells i.p.
Therapy: One injection i.p. on the day following implantation.
Termination: The animals are killed on the 8th day.
Evaluation: Weight of tumours of test animals compared with those of control animals.
Results:

| Compound | Dose (mg/kg) | Mortality | Tumour weight Treated/Control (%) |
|---|---|---|---|
| 1:1 | 500 | 0/12 | 1 |
| 2:11 | 1000 | 0/12 | 2 |

The following additional compounds exhibit anti-tumour activity in the foregoing test: 1:2–1:6, 1:14–1:17, 2:1–2:5, 3:1–3:3, and 3:9–3:10.

EXAMPLE 5

This example shows that compounds of the present invention, when being derived from a steroid having hormonal activity, still show this activity.

Many types of tumour in living animal bodies, e.g. breast cancer, prostatic cancer and leukemia, are sensitive to hormonal treatment. It is therefore a valuable property of the novel compounds that the steroid part of the molecule can be selected with relation to the kind of tumour which is to be treated.

The androgenic activity, as described below, is determined with established methods (see e.g. Dorfman, R.: Methods in Hormone Research, vol. II, Acad. Press, New York and London 1962, p. 275).

Experimental methods:

The androgenic effect is assayed in castrated male rats. Beginning two weeks after castration the animals are given one daily injection of the compound for 7 days. The weight of the ventral prostate is determined on the 8th day.

In preliminary experiments compounds 1:3, 1:11, and 1:12 show a considerable effect both after subcutaneous and intraperitoneal administration.

Thymolytic activity:

In preliminary experiments, invvestigating the thymolytic effect according to A. C. Hilger, Endocrine Bioassay Data, Part IV, Issue 2, May 1968 (assay 8), the compounds 1:15, 1:16, and 1:17 are found to have a significant activity.

Progestional activity:

The progestional activities of compounds 1:1, 1:2, 1:14, 2:2, and 2:11 are investigated in the Clauberg test using the prinicpal procedure as described by Elton and Edgren (Endocrinology 63 (1958) 464) and using the standard scale of McPhail (J. Physiol., London, 8 (1934) 145).

Preliminary experiments show that the compounds possess a considerable activity.

EXAMPLE 6

Manufacturing process for tablets a 10 mg
Model batch of 1000 tablets

| | | | |
|---|---|---|---|
| I | Compound 1:1, mesh*) 70 | 10.0 | g |
| | Lactosum, Ph. Nord. | 210 | g |
| | Amylum maidis, Ph. Nord. | 75 | g |
| II | Kollidon 25, B.A.S.F. | 3.5 | g |
| | Aqua purificata q.s. | | |
| III | Talcum, Ph. Nord. | 15 | g |
| | Magnesii stearas, Ph. Nord. | 1.5 | g |
| Weight of 1000 tablets: | | 315 | g |
| Weight of 1 tablet: 315 mg | | | |

*)The mesh standard is according to the international system of code DIN 4189/1968.

Punch: 10.5 mm round, flat, scored, bevel-edged.

Mix the screened substances I thoroughly and then moisten with II, whereupon the mixture is granulated through a stainless sieve No. 10 (mesh 25). Dry the granulate in an oven at a maximum temperature of 40° C., then repeat sieving through sieve No. 10. Add the substances under III and mix thoroughly. Punch tablets with a gross weight of about 315 mg.

EXAMPLE 7

Injectable solution 10 mg/ml

| | |
|---|---|
| Compound 2:2, mesh 70 | 10 mg |
| Benzyl alcohol | 80 mg |
| Peanut oil to make | 1 ml |

The substance is dissolved in the benzyl alcohol and peanut oil is added.

EXAMPLE 8

Vagitoria a 25 mg

| | |
|---|---|
| Compound 2:1 | 25 mg |
| Cacau butter | q.s. |

EXAMPLE 9

Ointment 2 %

| | | |
|---|---|---|
| Compound 1:14 | 2 | g |
| Triethanolamine | 1 | g |
| Glycerol | 7 | g |
| Cetanol | 2.5 | g |
| Lanoline | 2.5 | g |
| Stearic acid | 20 | g |
| Sorbitan monooleate | 0.5 | g |
| Sodium hydroxide | 0.2 | g |
| Methyl paraben | 0.3 | g |
| Propyl paraben | 0.1 | g |
| Ethanol | 0.9 | g |
| Water to make | 100 | g |

EXAMPLE 10

| Capsules a 10 mg | |
| --- | --- |
| Compound 1:2 | 10 mg |
| Magnesium stearate | 2 mg |
| Talcum | 188 mg |

The substances are mixed and filled in capsules.

In the foregoing Examples 6–10 relating to compositions the compounds are named according to the number code defined in Example 4. The Examples 6–10 are merely representative with regard to active ingredients exemplified. It is to be understood that other compounds disclosed in the foregoing Examples 1–3 may also be substituted for the active ingredients illustrated in the above examples.

Also, it is to be noted that two or more compounds of the invention may be used in combination in the compositions illustrated, and also, if desired, in combination wit other pharmacologically active agents.

Various modifications and equivalents will be apparent to one skilled in the art and may be used in the compounds, compositions and methods of the present invention without departing from the spirit or scope thereof, and it is therefore to be understood that the invention is not to be limited to the specific examples and embodiments disclosed herein.

References

1. McOmie, J. F. W. Protective Groups in Organic Chemistry. Plenum Press, London 1973.
2. Djerassi, C. Steroid Reactions. Holden-Day, San Francisco 1963, chapter 1.
3. Hermann, W. O., Baum, E., and Haehnel, W. German Pat. No. 654,282 (1937), CA 32, 2148$^9$ (1938).
4. Toussaint, W. J. and MacDowell, L. G. U.S. Pat. No. 2,299,862 (1942); Adelman, R. L. J. Org. Chem. 14 (1949) 1057.
5. Brandstrom, A. Preparative Ion Pair Extraction. Apotekarsocieteten/Hässle Läkemedel, Sweden 1974, p. 109.
6. Sandler, S. R. and Karo, W. Organic Functional Group Preparations. Academic Press, New York 1971, p. 252.
7. Bruson, H. A. in Adams, R. (Ed.). Organic Reactions vol. V (1949) 79.
8. Sulzbacher, M., Bergmann, E. D., and Pariser, E. R. J. Amer. Chem. Soc. 70 (1948) 2827.
9. Rosenkranz, G. J., Pataki, J., and Djerassi, C. J. Org. Chem. 17 (1952) 290.
10. Fieser, L. F. J. Amer. Chem. Soc. 76 (1954) 1945.
11. Mazur, R. H. and Brown, E. A. J. Amer. Chem. Soc. 77 (1955) 6670.
12. Corey, E. J. and Mitra, R. B. J. Amer. Chem. Soc. 84 (1962) 2938.
13. Wunsch, E. in Müller E. (Ed.). Methoden der organischen Chemie (Houben-Weyl). Band XV/1, p. 47.
14. Levin, Y., Berger, A., and Katchalski, E. Biochem. J. 63 (1956) 308.
15. Baer, E., Maurukas, J., and Russell, M. J. Amer. Chem. Soc. 74 (1952) 152.
16. Haas, H. J. Chem. Ber. 94 (1961) 2442.
17. Corey, E. J. and Venkateswarlu, A. J. Amer. Chem. Soc. 94 (1972) 6190.
18. Corey, E. J. and Bock, M. G. Tetrahedron Letters 38 (1975) 3269.

We claim:

1. Novel compound having the general formula

St—R wherein R is

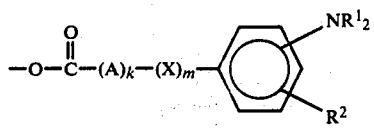

where $R^1$ is a β- or γ-halogensubstituted alkyl group having 2 to 4 carbon atoms, the halogen being chlorine or bromine;

where $R^2$ is selected from the group consisting of hydrogen, lower alkyl, lower alkoxy, and halogen;

where A is a straight hydrogen chain having at most 4 carbon atoms and being saturated or containing one double bond, at most 2 hydrogen atoms of A being replaced by lower alkyl and at most one of the hydrogen atoms situated at the carbon atom adjacent to a

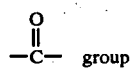

being replaced by a group selected from the group consisting of amino and lower alkanoylamino;

where X is selected from the group consisting of —O— and —S—;

where k and m are independently selected from the group consisting of zero and one, k always being one when m is one; wherein St is the radical of a steroid having a cyclopentanophenanthrene carbon-carbon skeleton containing up to a maximum of 40 carbon atoms, inclusive of substituents, said radical including the carbon-carbon skeleton of a steroid nucleus which is an unsaturated gonane nucleus having up to a maximum of three double bonds, said steroid radical being attached to R at the 3-position thereof, said position wherein said steroid is attached to R always being situated at the end of an olefinic bond of said gonane nucleus, said position being identified according to steroid nomenclature, selected from such compounds wherein said radical, St, of a steroid as defined above, has a carbon-carbon skeleton selected from the group consisting of: the carbon-carbon skeletons of estra-3,5-diene, estra-3,5(10)-diene, 5α-androst-2-ene, 5α-androst-3-ene, androsta-3,5-diene, pregna-3,5-diene, pregna-1,3,5-triene, and pregna-3,5,7-triene, and such compounds wherein a hydroxyl group connected to a non-olefinic carbon atom of the steroid skeleton of St, that is a non-enolic hydroxyl group, is esterified with an acid selected from the group consisting of alkane monocarboxylic acids having at most ten carbon atoms, alkane dicarboxylic acids having at most four carbon atoms, aromatic carboxylic acids having at most ten carbon atoms, and inorganic polybasic acids, and wherein one or more of the remaining free acid group or groups of any such polybasic acid is in the free form, in the form of a salt thereof with a pharmaceutically acceptable cation, or etherified with an alcohol selected from the group consisting of aliphatic and cycloaliphatic alcohols having at most six carbon atoms.

2. A compound according to claim 1,
wherein said steroid radical has a nucleus selected from the group consisting of
3,17β-dihydroxyestra-3,5-diene,
3-hydroxyestra-3,5-dien-17-one,
3,17β-dihydroxyestra-3,5(10)-diene,
3-hydroxyestra-3,5(10)-dien-17-one,
3,17β-dihydroxy-5α-androst-2-ene,
3-hydroxy-5α-androst-2-en-17-one,
3,17β-dihydroxy-5α-androst-3-ene,
3-hydroxy-5α-androst-3-en-17-one,
3,17β-dihydroxyandrosta-3,5-diene,
3,11β,17β-trihydroxyandrosta-3,5-diene,
3-hydroxyandrosta-3,5-dien-17-one,
3-hydroxy-5α-pregn-3-en-20-one,
3,17-dihydroxy-17α-pregna-3,5-diene,
3-hydroxypregna-3,5-dien-20-one,
3,17-dihydroxypregna-3,5-dien-20-one,
3,21-dihydroxypregna-3,5-dien-20-one,
3,11β,21-trihydroxypregna-3,5-dien-20-one,
3,11β,17,21-tetrahydroxypregna-3,5-dien-20-one,
3,11β,16α,17,21-pentahydroxypregna-3,5-dien-20-one,
3,21-dihydroxypregna-3,5-dien-11,20-dione,
3,17,21-trihydroxypregna-3,5-dien-11,20-dione,
3,17-dihydroxy-17α-pregna-3,5-dien-20-yne,
3,11β,17,21-tetrahydroxypregna-1,3,5-trien-20-one,
3,11β,16α,17,21-pentahydroxypregna-1,3,5-trien-20-one,
3,17,21-trihydroxypregna-1,3,5-trien-11,20-dione, and
3,17-dihydroxypregna-3,5,7-trien-20-one and
wherein said steroid radical, St, has the said steroid nucleus with a hydroxyl group removed from the 3-position thereof, the said radical, R, being attached to said steroid nucleus at said position.

3. A compound according to claim 2,
wherein any further substitution present in the carbon-carbon skeleton of said steroid nucleus, being at most a trisubstitution, wherein the positions of the steroid carbon-carbon skeleton which are substituted are selected from the positions consisting of the 1,2-, 4-, 6-, 9-, 16-, 17-, 18-, and 21-positions, where the substitution, if any, comprises at least one substituent selected from the group consisting of methyl, ethyl, methylene, allyl, ethynyl, fluoro, and chloro.

4. A compound according to claim 3,
wherein $R^1$ is a β-halogen substituted alkyl group, selected from the group consisting of β-halogen substituted ethyl, n-propyl, and n-butyl;
wherein $R^2$ is hydrogen or lower alkyl;
wherein m is zero;
wherein the group —$NH^1_2$ is in m- or p-position when k is zero and in p-position when k is one;
wherein $R^2$, when the group —$NR^1_2$ is in m-position, is in p-position; and
wherein A, when substituted with an amino or a lower alkanoylamino group, is a saturated hydrocarbon chain containing two carbon atoms.

5. A compound according to claim 4,
wherein $R^1$ is β-chloroethyl.

6. A compound according to claim 5,
wherein said steroid nucleus is selected from the group consisting of
3,17β-dihydroxyestra-3,5-diene,
3,17β-dihydroxy-5α-androst-2-ene,
3,17β-dihydroxyandrosta-3,5-diene, and
3,11β,17β-trihydroxyandrosta-3,5-diene nuclei;
any further substitution in the carbon-carbon skeleton of said steroid nucleus being based on substitution in a position selected from the group consisting of the 9- and 17-positions and with a substituent selected from the group consisting of methyl and fluoro.

7. A compound according to claim 5,
wherein said steroid nucleus is selected from the group consisting of
3,17β-dihydroxyestra-3,5-diene,
3,17β-dihydroxyestra-3,5(10)-diene,
3-hydroxypregna-3,5-dien-20-one, and
3,17-dihydroxypregna-3,5-dien-20-one nuclei;
and further substitution in the carbon-carbon skeleton of said steroid nucleus being based on substitution in a position selected from the group consisting of the 6- and 17-positions and with a substituent selected from the group consisting of methyl, ethynyl, and chloro.

8. A compound according to claim 5,
wherein said steroid nucleus is selected from the group consisting of
3,21-dihydroxypregna-3,5-dien-20-one,
3,11β,17,21-tetrahydroxypregna-3,5-dien-20-one,
3,17,21-trihydroxypregna-3,5-dien-11,20-dione,
3,11β,17,21-tetrahydroxypregna-1,3,5-trien-20-one,
3,11β,16α,17,21-pentahydroxypregna-1,3,5-trien-20-one, and
3,17,21-trihydroxypregna-1,3,5-trien-11,20-dion nuclei;
and further substitution in the carbon-carbon skeleton of said steroid nucleus based on substitution in position selected from the group consisting of the 9- and 16-positions and with a substituent selected from the group consisting of methyl and fluoro.

9. A compound according to claim 6,
wherein said steroid radical, St, is selected from the group consisting of
17β-hydroxyestra-3,5-diene,
17β-hydroxy-5α-androst-2-ene,
17β-hydroxyandrosta-3,5-diene,
17β-hydroxy-17α-methylandrosta-3,5-diene, and
9α-fluoro-11β,17β-dihydroxy-17α-methylandrosta-3,5-diene radicals.

10. A compound according to claim 7,
wherein said steroid radical, St, is selected from the group consisting of
17α-ethynyl-17β-hydroxyestra-3,5-diene,
17α-ethynyl-17β-hydroxyestra-3,5(10)-diene,
pregna-3,5-dien-20-one, and
17-hydroxypregna-3,5-dien-20-one radicals.

11. A compound according to claim 8,
wherein said steroid radical, St, is selected from the group consisting of
21-hydroxypregna-3,5-dien-20-one,
17,21-dihydroxypregna-3,5-dien-11,20-dione,
11β,17,21-trihydroxypregna-3,5-dien-20-one,
17,21-dihydroxypregna-1,3,5-trien-11,20-dione,
11β,17,21-trihydroxypregna-1,3,5-trien-20-one,
9α-fluoro-11β,17,21-trihydroxy-16α-methylpregna-1,3,5-trien-20-one,
9α-fluoro-11β,17,21-trihydroxy-16β-methylpregna-1,3,5-trien-20-one, and
9α-fluoro-11β,16α,17,21-tetrahydropregna-1,3,5-trien-20-one radicals.

12. A compound according to claim 4, selected from the group consisting of

3-/3-(N,N-bis(2-bromoethyl)amino)-4-methylbenzoyloxy/-17β-hexanoyloxy-4-methylandrost-3-ene, and 11β,17,21-triacetoxy-3-/3-(N,N-bis(2-chloropropyl)amino)-4-methylbenzoyloxy/-9α-fluoro-16β-methylpregna-1,3,5-trien-20-one.

13. A compound according to claim 1, selected from the group consisting of

17β-acetoxy-3-/4(N,N-bis(2-chloroethyl)amino)-phenyl)-acetoxy/androsta-3,5-diene, 17β-acetoxy-3-/3-(4-(N,N-bis(2-chloroethyl)amino)-phenoxy)propanoyloxy/-17α-methylandrosta-3,5-diene, 3-[4-(4-(N,N-bis(2-chloroethyl)amino)phenyl)-butanoyloxy]-17β-propanoyloxyestra-3,5-diene, 17β-acetoxy-3-[4-(4-(N,N-bis(2-chloroethyl)amino)-phenyl)butanoyloxy]androsta-3,5-diene, 17β-acetoxy-3-[4-(4-(N,N-bis(2-chloroethyl)amino)-phenyl)butanoyloxy]5αandrost-2-ene, 3-[(2S)-2-acetamido-3-(4-(N,N-bis(2-chloroethyl)amino)phenyl)propanoyloxy]-17β-propanoyloxyandrosta-3,5-diene, and 3-[3-(N,N-bis(2-chloroethyl)amino)-4-methylbenzoyloxy]androsta-3,5-diene-17β-phosphate.

14. A compound according to claim 1, selected from the group consisting of 17-acetoxy-3-/4-(4-(N,N-bis(2-chloroethyl)amino)-phenyl)butanoyloxy/pregna-3,5-dien-20-one, 3-/4-(4-(N,N-bis(2-chloroethyl)amino)phenyl)-butanoyloxy/pregna-3,5-dien-20-one, 17β-acetoxy-3-/3-(2-(N,N-bis(2-chloroethyl)amino)-phenyl)propenoyloxy/-17α-ethynyl-18-methylestra-3,5-diene, 17-acetoxy-3-[4-(N,N-bis(2-chloroethyl)amino)-phenylacetoxy]pregna-3,5-dien-20-one, 17β-acetoxy-3-/4-(4-(N,N-bis(2-chloroethyl)amino)-phenyl)butanoyloxy/-17α-ethynylestra-3,5-diene, and 17-acetoxy-3-[3-(N,N-bis(2-chloroethyl)amino)-4-methylbenzoyloxy]-pregna-3,5-dien-20-one.

15. A compound according to claim 1, selected from the group consisting of 21-acetoxy-3-[2-(4-(N,N-bis(2-chloroethyl)amino)-phenyl)-2-methylpropanoyloxy]-6-fluoro-11β-hydroxy-16α,17-isopropylidendioxypregna-3,5-dien-20-one, 17,21-diacetoxy-3-[4-(4-(N,N-bis(2-chloroethyl)amino)-phenyl)butanoyloxy]-pregna-3,5-dien-11,20-diene, 17,21-diacetoxy-3-[4-(4-(N,N-bis(2-chloroethyl)amino)-phenyl)butanoyloxy]-pregna-3,5-dien-20-one, and 21-acetoxy-3-[4-(4-(N,N-bis(2-chloroethyl)amino)-phenyl)butanoyloxy]-pregna-3,5-dien-20-one.

16. A composition of matter comprising as an active ingredient a compound according to claim 1 in combination with a pharmaceutically acceptable carrier.

17. A method of treating a living animal body suffering from a disorder responsive to treatment with anticancer agents and with immunosuppressive agents comprising administering a compound of claim 1 to said animal body in an amount effective for alleviation of said disorder.

18. The composition of claim 16 wherein the active ingredient is a compound according to claim 11 present in an amount between about 0.05 and 15 percent by weight of the composition.

* * * * *

UNITED STATES PATENT AND TRADEMARK OFFICE
CERTIFICATE OF CORRECTION

PATENT NO. : 4,150,126

DATED : April 17, 1979

INVENTOR(S) : Fex et al.

It is certified that error appears in the above-identified patent and that said Letters Patent are hereby corrected as shown below:

Col. 3, line 45; "$NR_2^1$" should read -- $NR^1_2$ --

Col. 3, line 49; "$NR_2^1$" should read -- $NR^1_2$ --

Col. 5, line 19; "consistng" should read -- consisting --

Col. 7, line 68; "structures" should read -- structure --

Col. 8, first formula; (II)

Col. 8, second formula; (V)

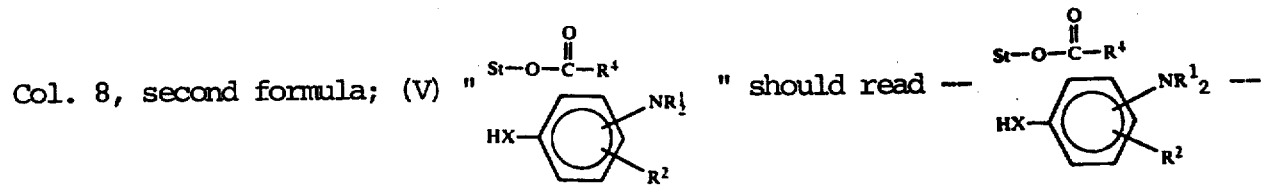

UNITED STATES PATENT AND TRADEMARK OFFICE
CERTIFICATE OF CORRECTION

PATENT NO. : 4,150,126
DATED : April 17, 1979
INVENTOR(S) : Fex et al.

It is certified that error appears in the above-identified patent and that said Letters Patent are hereby corrected as shown below:

Col. 9, line 5; "regenrated" should read -- regenerated --
Col. 9, line 8; "methylthiomethyleters" should read
 -- methylthiomethylethers --
Col. 9, line 35; "11-3" should read -- 1-3 --
Col. 9, line 67; "inorlganic" should read -- inorganic --
Col. 12, lines 12 & 13; Col. 12, lines 34 & 35; Col. 12, lines 39 & 40;
 Col. 12, lines 42 & 43; Col. 13, lines 21 & 22; Col. 13, lines 25 & 26;
 Col. 13, lines 58 & 59; Col. 13, lines 66 & 67; Col. 14, lines 4 & 5; and
 Col. 21, lines 20 & 21; In each of these places, "(2-chloroethyl-
        )amino)" should read
 -- (2-chloroethyl)-
    amino) --     (The second parenthesis should be on the same line
                    as the first parenthesis)
Col. 13, line 3; "-3/4-(4-" should read -- -3-/4-(4- --
Col. 13, lines 61 & "(2-chloropropyl-   should read  -- (2-chloropropyl)-
        62    )amino)"                                  amino) --
(The second parenthesis should be on the same line as the first parenthesis)
Col. 14, lines 1 & "(2-bromoethyl-   should read -- (2-bromoethyl)amino) --
         2    )amino"
(The second parenthesis should be on the same line as the first parenthesis)

Col. 11, line 63; "siginficant" should read -- significant --
    Col. 13, line 49; "5H,H-4+H-6++H-7+CH$_2$-16)," should read
      -- 5H,H-4+H-6+H-7+CH$_2$-16), --
    Col. 14, line 28; "comound" should read -- compound --
    Col. 16, line 1; "prinicpal" should read -- principal --

UNITED STATES PATENT AND TRADEMARK OFFICE
CERTIFICATE OF CORRECTION

PATENT NO. : 4,150,126

DATED : April 17, 1979

INVENTOR(S) : Fex et al.

It is certified that error appears in the above-identified patent and that said Letters Patent are hereby corrected as shown below:

Col. 14, Table 1, line 56, second column from the left; "5 33 150" should read -- 5 x 150 --
Col. 15, line 61; "invvestigating" should read -- investigating --
Col. 17, line 22; "wit" should read -- with --
Col. 19, line 55; "—$NH^1_2$" should read -- —$NR^1_2$ --
Col. 20, line 32; "nucleus based" should read -- nucleus being based --
Col. 20, line 32; "in position" should read -- in a position --  Response and Amendment dated September 5, 1978, page 4, line 14.
Col. 20, line 65; "-tetrahydropregna-" should read -- -tetrahydroxypregna- --
Col. 21, lines 4 & 5 "(2-chloropropyl-)amino)" should read -- (2-chloropropyl)amino) --
(The second parenthesis should be on the same line as the first parenthesis)
Col. 21, line 27; "/4-(4-(N,N-" should read -- /4-(4-N,N- --
Col. 22, line 7; "methylbenzoyloxy]-pregna" should read -- methylbenzoyloxy] pregna --

Signed and Sealed this

Twenty-eighth Day of August 1979

[SEAL]

Attest:

LUTRELLE F. PARKER

*Attesting Officer*   *Acting Commissioner of Patents and Trademarks*